United States Patent
Mikus et al.

[11] Patent Number: 5,928,217
[45] Date of Patent: Jul. 27, 1999

[54] UROLOGICAL STENT THERAPY SYSTEM AND METHOD

[75] Inventors: Paul Mikus, Aliso Viejo; William Moseley, San Diego, both of Calif.

[73] Assignee: Endocare, Inc., Irvine, Calif.

[21] Appl. No.: 09/179,598

[22] Filed: Oct. 26, 1998

Related U.S. Application Data

[63] Continuation of application No. 08/629,650, Apr. 9, 1996, Pat. No. 5,830,179.

[51] Int. Cl.$^6$ .................................................... A61M 31/00
[52] U.S. Cl. ............................................ 604/530; 604/531
[58] Field of Search .................................... 604/530, 531, 604/104–109, 500; 606/108, 191–194, 198

[56] References Cited

U.S. PATENT DOCUMENTS

| | | | |
|---|---|---|---|
| 4,170,990 | 10/1979 | Baumgart et al. | 128/92 |
| 4,490,311 | 12/1984 | Ruiz | 128/303.1 |
| 4,503,569 | 3/1985 | Dotter | 3/1.4 |
| 4,512,338 | 4/1985 | Balko et al. | 128/1 R |
| 4,733,665 | 3/1988 | Palmaz | 128/343 |
| 4,762,128 | 8/1988 | Rosenbluth | 128/343 |
| 4,795,458 | 1/1989 | Regan | 623/1 |
| 4,969,890 | 11/1990 | Sugita | 606/192 |
| 5,037,427 | 8/1991 | Harada et al. | 606/108 |
| 5,078,736 | 1/1992 | Behl | 623/1 |
| 5,089,005 | 2/1992 | Harada et al. | 606/194 |
| 5,147,370 | 9/1992 | McNamara et al. | 606/108 |
| 5,178,618 | 1/1993 | Kandarpa | 606/28 |
| 5,197,978 | 3/1993 | Hess | 623/1 |
| 5,224,953 | 7/1993 | Morgantaler | 606/192 |
| 5,246,445 | 9/1993 | Yachia et al. | 606/108 |
| 5,323,778 | 6/1994 | Kandarpa | 128/653.2 |
| 5,466,242 | 11/1995 | Mori | 606/198 |
| 5,830,179 | 11/1998 | Minkus et al. | 604/530 X |

FOREIGN PATENT DOCUMENTS 0 626 153 A1  11/1994  European Pat. Off.

OTHER PUBLICATIONS

Instent, Prostacoil™, undated Brochure.
Terai, et al., Transurethral Microwave Thermotherapy for BPH, 2 Int. J. Urol 24 (1995).
Cragg, et al., Percutaneous Arterial Grafting, 150 Radiology 45 (Jan. 1984).

*Primary Examiner*—John D. Yasko
*Attorney, Agent, or Firm*—Crockett & Fish; K. David Crockett, Esq.

[57] ABSTRACT

A stent system and method for use in the prostate gland. The stent is made of a shape memory alloy such as nitinol, and has a low temperature martensite state, with a martensite transition temperature below body temperature, and a high temperature austenite state, with an austenite transition temperature at or above body temperature, and a memorized shape in the high temperature austenite state which is a helical coil of diameter large enough to hold the prostatic urethra open. The stent is used to heat the prostate and is left in the prostatic urethra while the prostate heals. After the prostate is substantially healed, the stent is cooled to its martensite state and is easily removed from the urethra.

3 Claims, 6 Drawing Sheets

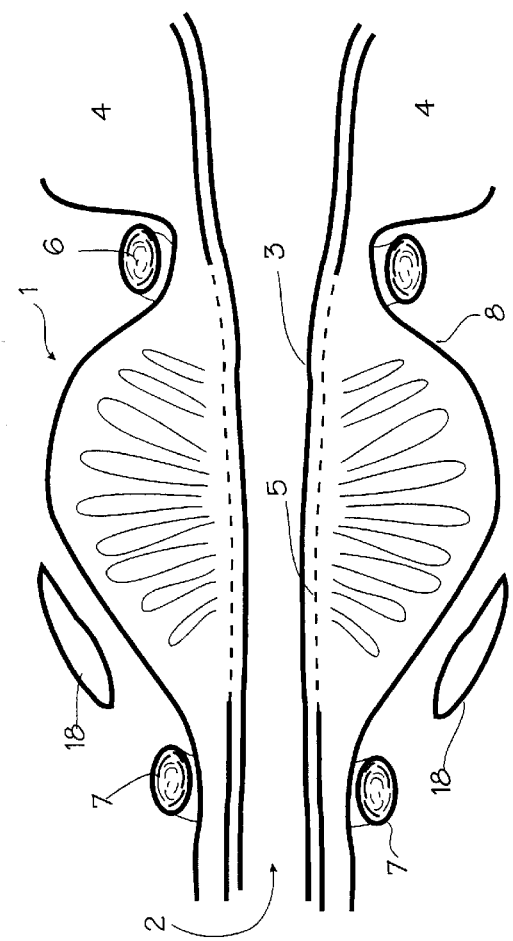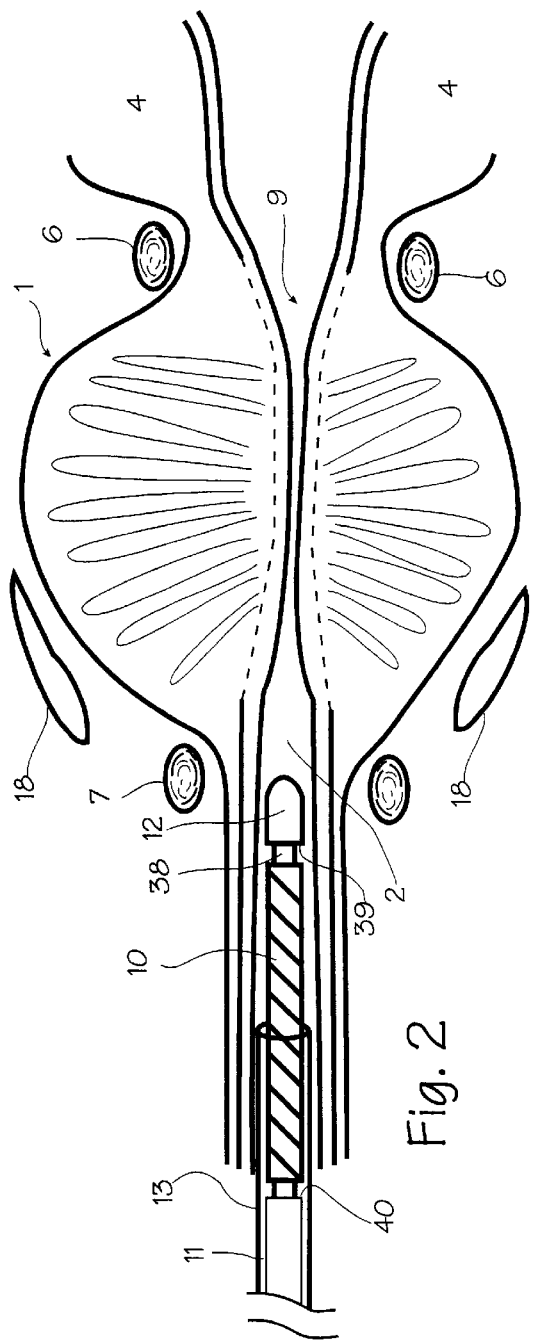

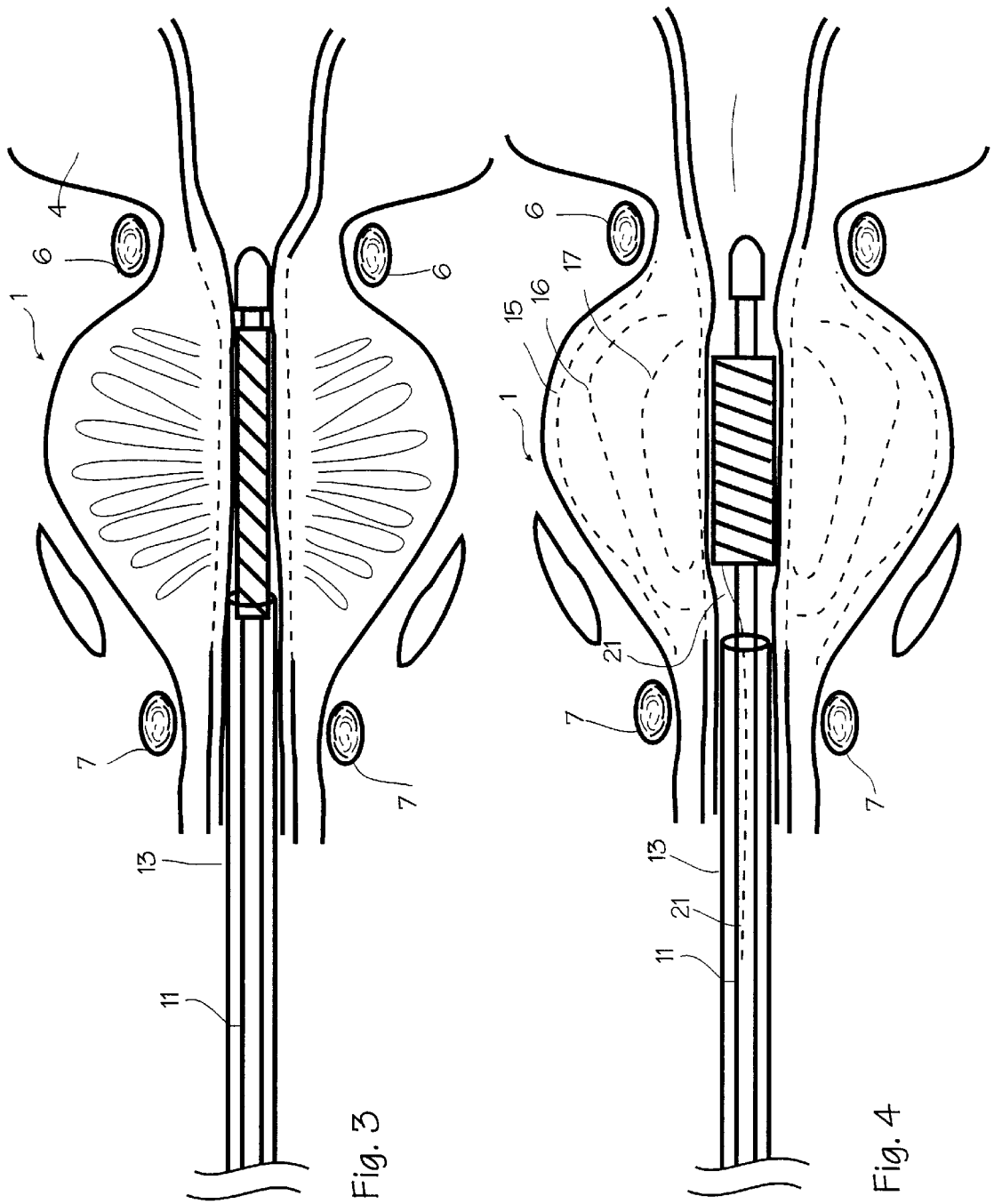

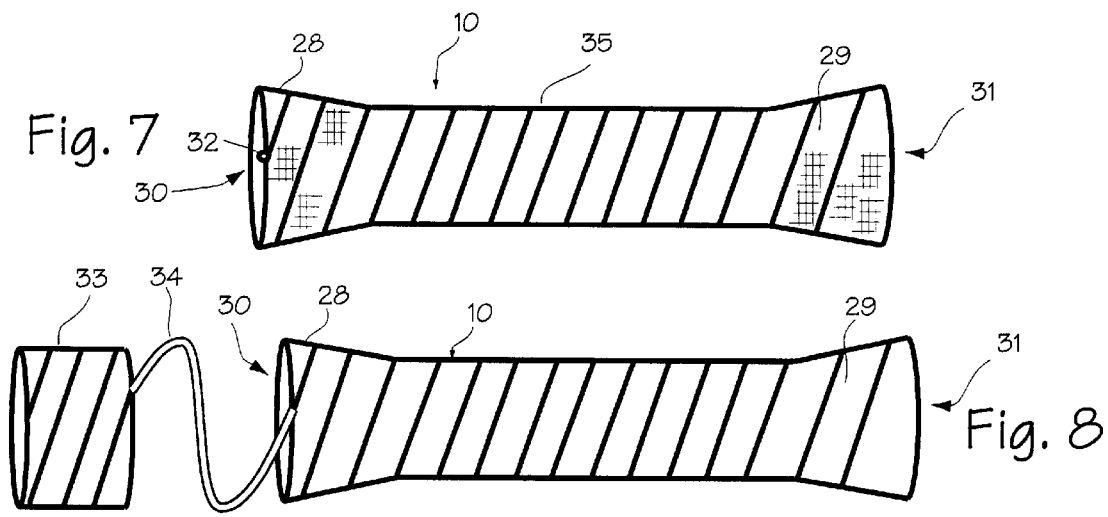
Fig. 7
Fig. 8
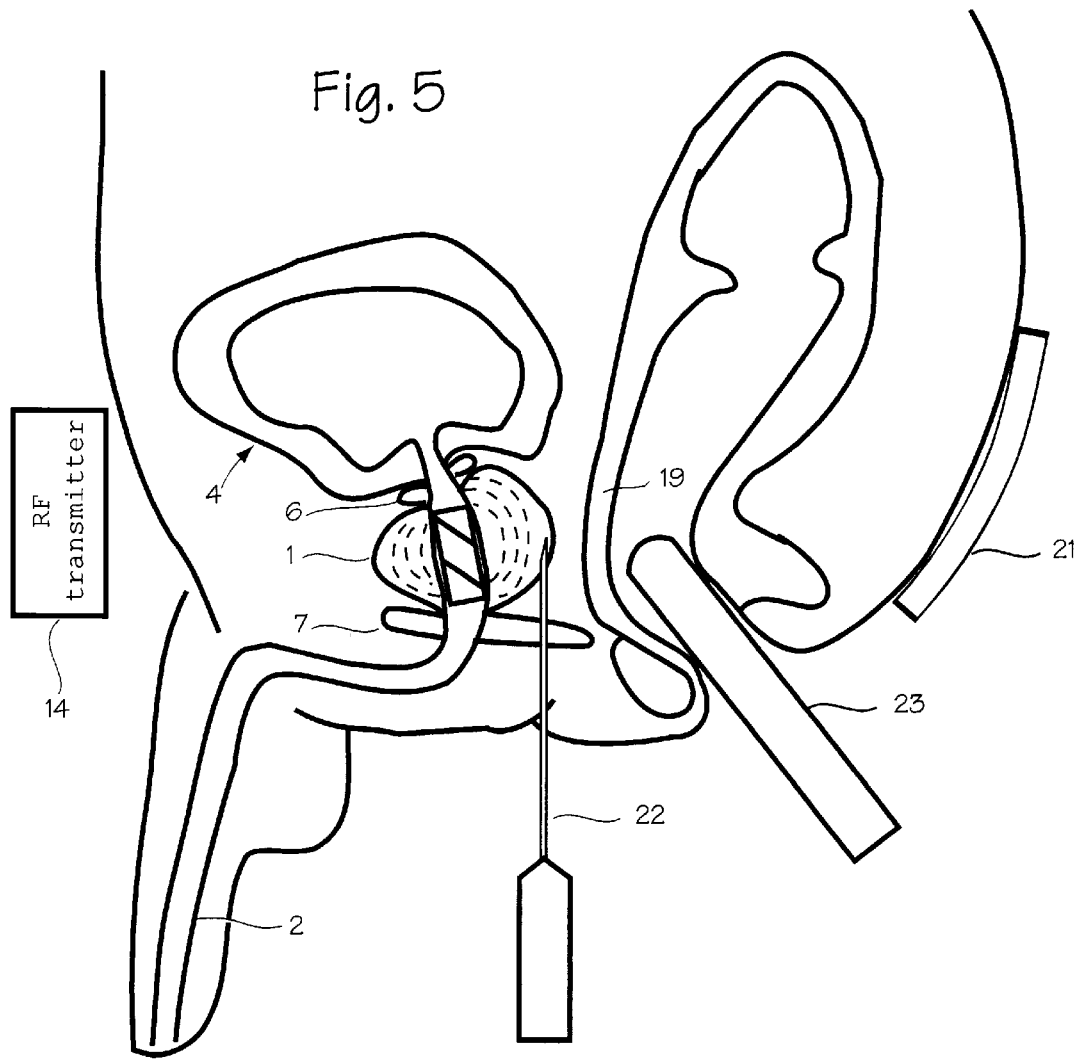
Fig. 5

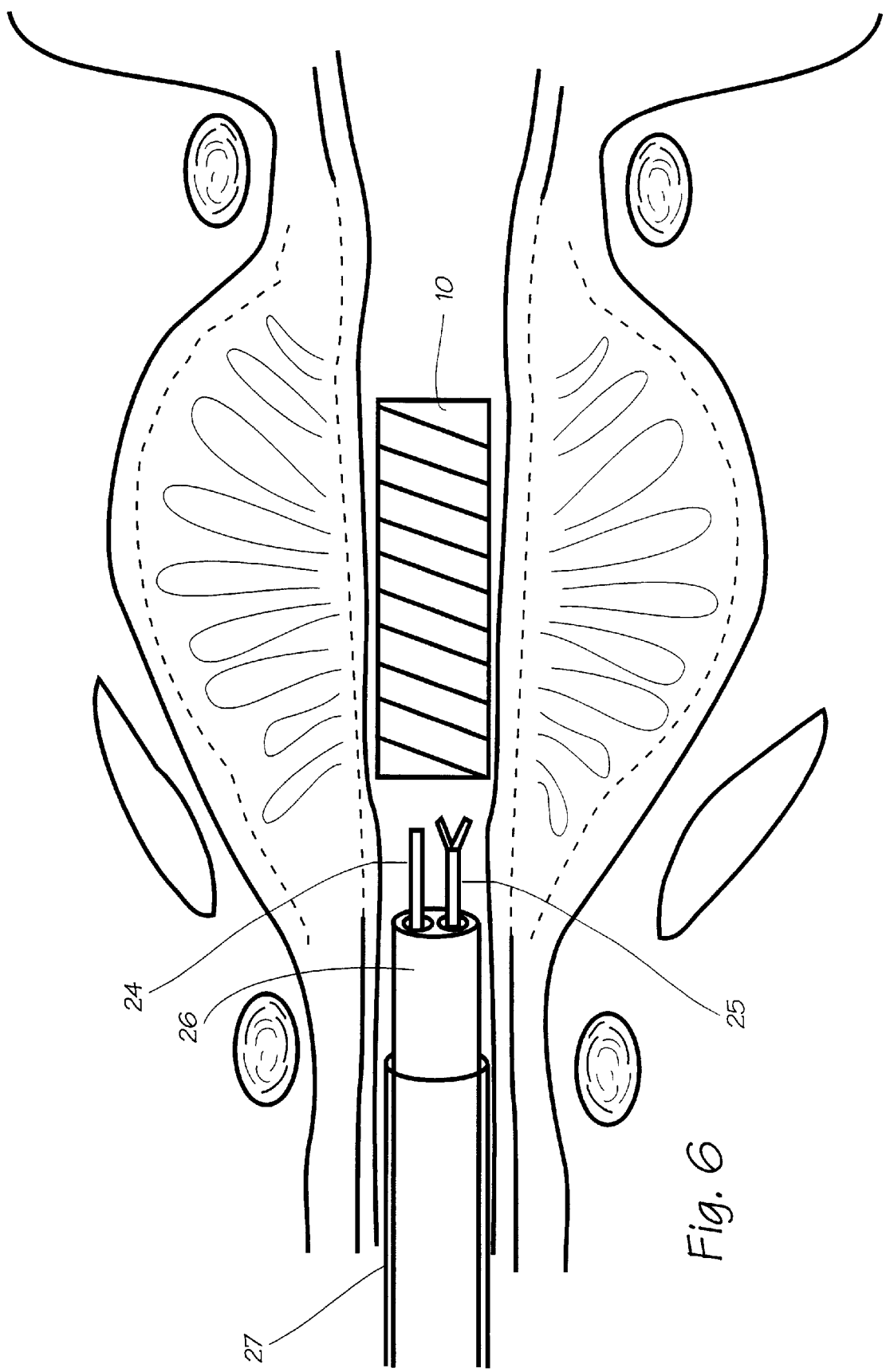

UROLOGICAL STENT THERAPY SYSTEM AND METHOD

This application is a continuation of U.S. application Ser. No. 08/629,650 filed Apr. 9, 1996, now U.S. Pat. No. 5,830,179.

FIELD OF THE INVENTION

This invention relates to stents, urology, and treatments for benign prostate hypertrophy or prostate cancer, as well as methods for correction of vessel occlusions.

BACKGROUND OF THE INVENTION

The inventions described below were developed to aid in the treatment of prostate enlargement and/or prostate cancer. Prostate enlargement, also known as benign prostate hyperplasia or benign prostate hypertrophy, is a common affliction among older men. The condition involves swelling of the prostate. The prostate surrounds the urethra, or urinary tract, and swelling of the prostate prevents passage of urine from the bladder. Benign prostate hyperplasia is uncomfortable because it makes urination difficult or impossible, The condition is also dangerous because it can lead to infection of the bladder and kidneys, and severe cases may lead to death.

Prostate cancer is also a common affliction among older men, and may lead to many of the same symptoms as benign prostate enlargement. Prostate cancer is more dangerous in that it may spread to other organs and is often fatal. Early treatment can reduce the risks of death due to prostate cancer.

A surgical cure for prostate enlargement is called resection. Resection can be accomplished by cutting away a large portion of the prostate gland. The operation can be performed by cutting through the skin to expose the prostate gland, and using scalpels to cut into the prostate. Preferably, resection is accomplished from inside the urethra, using a resectoscope inserted through the penis. The resectoscope includes an endoscope for visual observation and a resecting loop which a surgeon uses to scrape and gouge away the prostate gland from the inside.

Prostate enlargement can be treated with heat treatments such as hyperthermia or thermotherapy, cold treatment (hypothermia or cryotherapy), and ablation. It has long been known that heating a swollen prostate gland can lead to a decrease in swelling and eventual relief from the condition. Heat treatment denaturizes the proteins in the prostate tissue, like a slow cooking of the tissues. The biological effects of heat treatment and the appropriate thermal dosage are discussed in more detail in articles such as Terai, et al., Transurethral Microwave Thermotherapy For Benign Prostatic Hyperplasia, International Journal of Urology 24 (March 1995) and Pow-Sang, et al., Thermocoagulation Effect Of Diode Laser Radiation In The Human Prostate, 45 Urology 790 (May 1995), but it is sufficient for the purposes of this disclosure to understand that application of heat at sufficiently high temperature for sufficient lengths of time to destroy some or all cells in a portion of the prostate gland eventually produces a therapeutic effect.

Devices for heating the prostate are illustrated, for example, in Edwards, et al., Medical Probe Device and Method, U.S. Pat. No. 5,366,490 (Nov. 22, 1994), which shows a device for application of RF or microwave energy into the prostate while protecting the prostatic urethra from damage during the treatment. Hyperthermia treatment, as the term is generally used, is accomplished in the temperature range of 40–60° C. Thermotherapy, as the term is generally used, is accomplished by heating the prostate above 60° C. Both heat treatments have been beneficially used in the treatment of prostate enlargement.

After heat treatment, the prostate gland will be partially destroyed. Thermal necrosis, thermocoagulation, denaturization, and other such terms are used to describe the thermal damage done to the prostate gland. The prostatic urethra will also be partially destroyed. The prostate gland and the prostatic urethra swell in response to the burn caused by the heat treatment, and this immediately causes acute blockage of the urethra. The prostate gland and prostatic urethra eventually heal, over several weeks or months, typically about three months after heat treatment.

During the healing period, much of the prostate and prostatic urethra that were damaged by the heat treatment are re-absorbed by the body through the blood vessels supplying the area. However, significant portions near the urethra slough off the urethra wall and fall into the urethra. Sloughing causes acute blockage of the urethra. Thus, during the post-operative healing period, swelling and sloughing cause acute blockage of the urethra, leading to extreme discomfort and clinical danger to the patient. After healing, the prostate will be smaller than before heat treatment and will not force closure of the urethra. The condition of benign prostate hyperplasia is essentially cured. Prostate cancer can also be treated successfully with similar heat treatments, usually in combination with chemotherapy or radiation treatment.

It has recently been proposed to use stents to support the urethra and keep it open despite pressure from the swollen prostate. The Prostacoil™ temporary intraprostatic stent, marketed by Instent, Inc. of Eden Prairie, Min., is an example of a stent adapted for use in the prostatic urethra. The stent includes an anchoring section and a prostatic section, and is placed with a delivery catheter shaft through the urethra. The stent is used long-term, for patients temporarily or permanently unfit for surgery.

A wide variety of stents have been proposed for use in various applications. Intravascular stents and coronary stents such as the Palmaz-Schatz stent illustrated in Palmaz, have been used to treat occlusions of blood vessels. A commonly suggested material for making stents is pseudoelastic and/or shape memory alloys such as Nitinol. For example, Sugita, Catheter, U.S. Pat. No. 4,969,890 (Nov. 13, 1990) proposes use of a shape memory alloy for an intravascular stent, and shows a device for percutaneous delivery of the stent to an occluded stenotic region of a blood vessel. Harada, et al, Method of Implanting a Stent Within a Tubular Organ of a Living Body and of removing Same, U.S. Pat. No. 5,037,427 (Aug. 4, 1991) proposes use of a two-way shape memory alloy stent in a blood vessel. Two-way shape memory is useful in a stent, according to Harada, to allow removal of the stent. As explained in Harada, it is not possible to remove a one-way shape memory stent after implantation. Harada proposes use of two-way shape memory stent with a hot, large diameter shape which holds a blood vessel open and a cold, small diameter shape which can be moved within the vessel and removed. Harada also discloses a device for percutaneous placement of the stent. Dotter, Transluminally Placed Expandable Graft Prosthesis, U.S. Pat. No. 4,503,569 shows the use of shape memory alloy stent proposed for use in blood vessels. Each of these references use saline solution injected through a catheter to control the temperature of the stent, thereby controlling the shape of the stent.

Stents may be left in blood vessels permanently, and are usually implanted for permanent use. The risk of infection around the stent in a blood vessel, or movement of the stent within a blood vessel, are somewhat limited by the environment. In the urethra, however, the risk of infection is high, and movement within the urethra may be caused by urination or ejaculation, especially if the prostate gland shrinks in response to treatment. Thus, there is a limit to the amount of time a stent may be left implanted in the urethra before infection sets in or migration occurs.

SUMMARY OF THE INVENTION

The devices described below include urological stents and devices for placing the stents in the urethra. Methods for treating benign prostate hyperplasia or prostate cancer with heat treatment, either hyperthermia or thermotherapy, using the stent as the heat source, are also described. Also, fabrication of the stent from a nitinol alloy, shape memory alloy, or pseudoelastic alloy, permits easy placement and subsequent removal of the stent, so that the stent may be placed in the urethra during the healing period and removed when no longer necessary. The inventions disclosed and claimed below combine various aspects of treatments discussed above and various new concepts to create new devices and methods for treating benign prostate hyperplasia.

BRIEF DESCRIPTION OF THE DRAWINGS

FIG. 1 is a cross-sectional view of the prostate gland with a stent in place.

FIGS. 2 through 4 are cross sectional views of an enlarged prostate illustrating use of the stent.

FIG. 5 is cross-sectional view of lower abdominal portion of the human body with a stent in place.

FIG. 6 is a cross-sectional view of the prostate gland with a stent in place and ready for removal.

FIGS. 7 and 8 are elevational views of the stent, with additional features for use within the prostatic urethra.

DETAILED DESCRIPTION OF THE INVENTION

Figure 10:
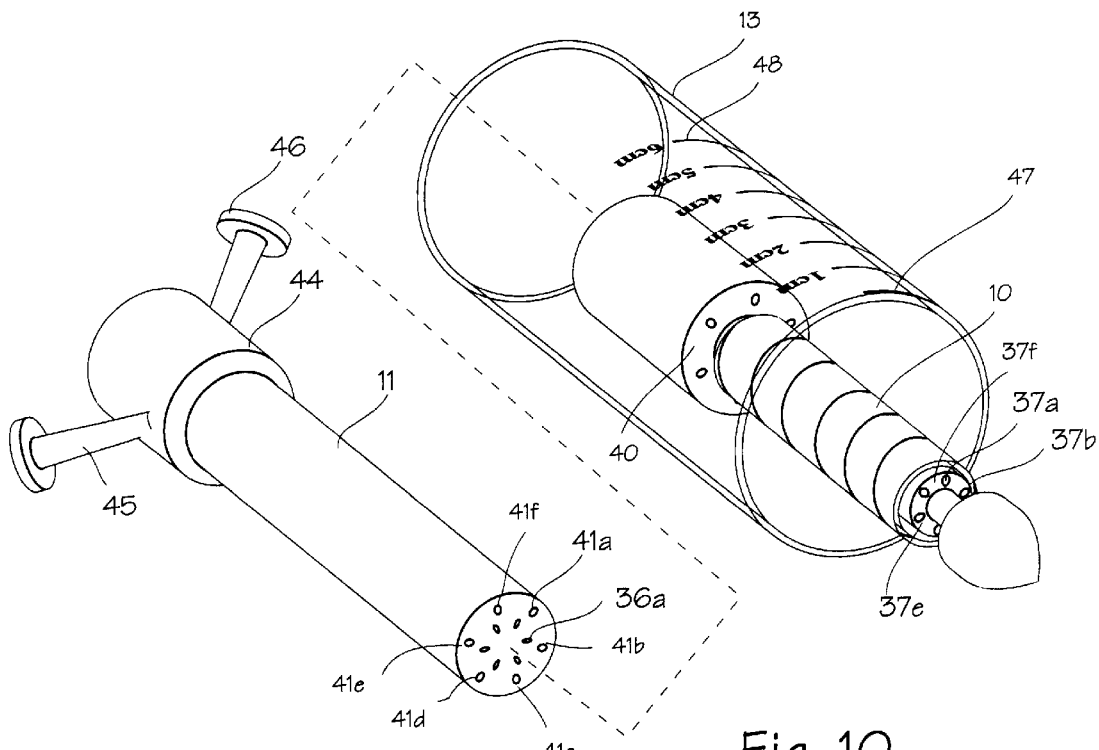
FIGS. 9 and 10 are elevational views of the stent delivery catheter for use with the present invention.

FIG. 1 shows a stent designed for use in the treatment of benign prostate hyperplasia or prostate cancer. The details of the local anatomy shown in this figure include the prostate gland 1, the urethra 2 and the prostatic urethra 3. The urethra is the channel which conducts urine from the bladder 4 to the penis for discharge from the body. The prostatic urethra is a continuation of the urethra, and it joins the prostate gland to the urethra. The boundary between the prostate gland and the prostatic urethra is ill defined, represented by the dashed line 5. The bladder neck sphincter 6 controls flow of urine from the bladder 4, and the external sphincter 7 controls flow of urine or ejaculate from the bladder 4 or prostate 1. The prostate capsule 8 surrounds the prostate gland. The prostate gland consists of various tissues, including glandular tissue (which produces ejaculate), muscular cells, and epithelial cells. The inside diameter of urethra 2 is typically about 2 centimeters, and the prostatic urethra varies in length from about 15 to 75 mm.

The condition of benign prostate hyperplasia causes the prostate to swell and close off the prostatic urethra, as illustrated in FIG. 2. The urethra 2 is squeezed shut by the swollen prostate, and has an occluded region 9. The stent 10 mounted on the distal portion of delivery catheter 11 with an atraumatic tip 12 is ready for placement in the occluded portion of the prostatic urethra. The stent is made of a nitinol alloy with a martensite transition temperature slightly below body temperature, in the range of 30–35° C. (this range is conveniently established or maintained with cold saline flow through the catheter or a catheter sheath). Thus, when the stent is cooled below body temperature by cold saline flow, it will enter the soft and pliable martensite state of the alloy. The chosen alloy has a wide hysteresis, so that it remains in the soft and pliable martensite state for a temperature range distinctly above the temperature at which it converts to martensite upon cooling. The transition temperature for the change to the austenitic state upon heating is slightly above body temperature, in the range of 38–60° C. or even higher, depending on the heating source used. When hot saline solution is used, 38–60° C. is convenient because that temperature range can be easily achieved by flushing hot saline through the catheter into the vicinity of the stent (100° C. is the equivalent to 212° F., the boiling point of water, so it can be appreciated that the temperature range or 38–60° C. is easily achieved in the operating room).

FIG. 2 depicts placement of the stent. The stent pictured in FIG. 2 has been cooled to accomplish the martensite transition, and the stent is soft and pliable. The stent is tightly wound around delivery catheter 11, and has a small diameter of about 1 cm that fits easily into the urethra 2. The catheter sheath 13 is provided to cover the stent during placement and provide a smooth outer surface to facilitate placement of the stent. The stent 10 is then pushed into the occluded region 9 of the prostatic urethra 3, as shown in FIG. 3. Preferably, the stent has an austenite transition temperature above body temperature, and there is no need to flush saline through the delivery catheter or sheath to keep the stent cooled below body temperature. Where the austenite transition temperature is at or below body temperature, the stent should be cooled with cold saline flow to maintain its martensite state until it is properly placed. Alternatively, the stent can be pseudoelastic or superelastic at body temperature, and in this case may be held in its small diameter shape by catheter sheath 13, in which case the sheath serves as a retaining mechanism for the stent.

After placement in a swollen prostate, as depicted in FIG. 3, the stent will be firmly held by the compressive forces of the prostate if swelling is severe enough, which it usually is in cases warranting intervention. Either during or after placement, the stent is flushed with hot saline which causes the stent to heat up above its austenite transition temperature. Of course, if the stent transition temperature is at or below body temperature, it will be sufficient to allow the stent to be heated to the austenite transition temperature by surrounding body temperature without injection of warm saline solution. Upon this transition, the stent recovers its original large diameter shape and forces the prostatic urethra open, as shown in FIG. 4. The stent may be left in the urethra for some time, but eventual infection is almost certain, so that heat therapy is accomplished according to the following description to ensure that the stent is needed for only a short period of time.

To heat the prostate, the stent is used as the heat source. Preferably, radiofrequency energy (RF energy) is broadcast from outside the body, from RF transmitter 14 as illustrated in FIG. 5. RF transmitters available from valley Labs of Boulder, Colo. capable of transmitting RF energy at powers of up to approximately 300 watts are sufficiently powerful to heat the stent and cause the stent reactively radiate RF energy into the prostate. The hot stent radiates heat into the prostate, and to some extent the reactive radiation from the stent heats prostate tissue. Radiation is maintained for an adequate length of time to heat a large portion of the prostate, indicated by dashed line 15 shown in FIG. 2, to 60° C. or more. FIG. 4 shows dashed line 15, which represents a thermocline of 60° C., and other isotherms of 70° C. (dashed line 16) and 80° C. (dashed line 17) are shown to illustrate the expected temperature gradient within the prostate during the heat therapy. Typical therapeutic treatments require approximately 10 to 40 minutes with the stent irradiated by 20 to 40 watts of RF energy to create temperatures of at least 40° C. (and preferably 60° C.) in the region to be destroyed. The heating may cause damage to a substantial portion of the prostate, but should avoid damage to surrounding tissues such as the neurovascular bundle 18 shown in FIGS. 1 and 2 and the colon 19 shown in FIG. 5.

During radiation, the stent may be grounded by attaching a ground wire 20 to the stent through the urethra. The ground wire is carried on the delivery catheter, and is releasably attached to the stent or merely in contact with the stent, so that the ground wire may be withdrawn while the stent is left in place. Alternatively, a grounding pad 21 can be placed on the skin near the prostate, providing a ground path through the body to the pad. The heating of the prostate can be monitored with one or more temperature probes 22 inserted through the skin in the transperineal area between the scrotum and the anus. Alternatively, heating may observed via ultrasound imaging through a transrectal ultrasound probe 23. The appearance of healthy and heat damaged prostate tissue may be differentiated on ultrasound images obtained through the ultrasound probe, and the progress of heat therapy can be monitored on the ultrasound displays provided by the ultrasound imaging system associated with the probe. The surgeon performing the therapy will decide when a sufficient portion of the prostate gland has been heat damaged so that eventual re-absorption of that damaged tissue will result in the cure of the condition. As an alternate to direct observation, surgeons may establish standard dosages of RF energy, in terms of wattage, frequency, and time, which ensure adequate heat treatment without danger of damage to surrounding organs, and may be applied without need to monitor thermal damage directly.

Alternate heating means may be employed. For example, the stent may be connected to a DC, AC or radiofrequency source through electrical connections running from the stent, through the delivery catheter, to an external power source. These sources can be used to heat the stent to temperatures sufficient for heat therapy. The same sources may be used for heating the stent to its shape recovery temperature.

After heating via the stent, the heated portion of the prostate gland swells and dies off. The prostatic urethra is also damaged by the treatment and swells and dies. Further occlusion of the urethra is prevented by the stent, which is left in place for some time after heat therapy. While the body's waste removal mechanisms re-absorb the destroyed prostate cells, the stent holds the urethra open and prevents sloughing of dead tissue into the urethra. Over several months, the body will re-absorb the portions of the prostate gland and prostatic urethra damaged by the heat therapy, and the enlargement will subside. During this healing time, the patient has benefited from the stent because it helps avoid the short term closure usually associated with heat therapy.

As the enlargement subsides, the prostate and prostatic urethra will subside from the stent, and the stent will become loose within urethra. The stent also presents an infection site, and if left in permanently will probably cause infection within the urethra. Thus, when the prostate gland has receded enough that the urethra will be patent upon removal of the stent, and before infection is likely to set in, the stent should be removed. The expected time frame for removal of the stent is two to three months after placement and heat therapy.

Removal of the stent is accomplished by inserting a catheter and flushing the stent with cold saline solution to cause reversion of the stent into the soft, pliable martensite state. As illustrated in FIG. 6, an endoscope 24 and endoscopic graspers 25 are them inserted through a catheter 26 to find and remove the stent. Because the stent is now soft and pliable, typically as easily deformable as silver solder, the stent can be grasped at its proximal end and pulled through the catheter. As the stent is pulled through the catheter, it unravels and deforms to easily fit through the catheter. Alternatively, the grasper can be used to hold the stent in place while the sheath 27 is gently pushed over the stent. The cold stent is soft and pliable and offers little resistance to the sheath.

When the stent is removed, the urethra is open, and the prostate is almost entirely healed. There may be some residual dead tissue throughout the prostate and the prostatic urethra, but this dead tissue will be removed without incident by the body, either through sloughing, which should occur without ill-effect through the now open urethra, or through continued re-absorption. At this stage, the condition of benign prostate enlargement has been cured.

A number of other features are added to the stent in order to optimize its use within the prostate, as illustrated in FIG. 7. Although destruction of the prostate gland is the desired goal, destruction of surrounding structures is undesirable. The bladder neck sphincter 6 and the external sphincter 7 control urine flow, and damage to these structures would lead to incontinence. To avoid thermal damage to the bladder neck sphincter and the external sphincter, the proximal end 28 and distal end 29 of the stent shown in FIG. 7 are thermally insulated to limit the heat transfer from the stent to the prostate gland at the distal and proximal ends of the stent. Insulating layers of PTFE (Teflon®) or other suitable plastics are sufficient to protect these structures.

The possibility of stent migration can be limited by providing flared ends on the stent. Flared ends 30 and 31 on the stent help to anchor it to the prostate gland and prevent slippage and migration of the stent. A small knob 32 is provided on the proximal end of the stent, attached to the end of the ribbon, and this provides for easier grasping of the stent when it is removed. An optional anchor section 33 and retaining wire 34 can be added to the stent, as shown in FIG. 8. The anchor section is spaced from the stent so that it resided downstream in the urethra and does not obstruct the external sphincter and is not subject to the RF energy used to heat the stent itself. The anchor section may also be thermally and electrically insulated to protect the urethra from any heat that might be conducted from the stent or caused by accidental irradiation from the RF source. The electrical and/or thermal insulation is shown in FIGS. 7 and 8 as the lightly cross hatched areas at either end of the stent.

Typical sizes for the stent are shown in FIG. 7 also. The stent is intended for use in the prostatic urethra 3, which varies in size from man to man. The length of the straight segment 35, when expanded, is about 3–5 cm. The diameter of the straight segment 35, when expanded, is about 2 cm. The length of the flared end portions is about 2 cm, with a diameter of 3 cm. Thus the overall length or the stent is about 7 to 9 cm. It may prove desirable to manufacture the stents in just a few standard sizes corresponding to commonly encountered prostate sizes, insofar as an exact size match is not usually necessary. If a non-standard size or an exact size is desired, stents may be specially manufactured to specification. Thus, variations of size beyond the sizes mentioned here may occasionally be needed and accomplished.

The stent will be inserted in its cold state, while it is pliable and easily deformed so that it may be tightly wrapped around the delivery catheter. The catheter diameter may be as small as the state of the art allows, but need only be small enough to fit comfortably into the urethra. Delivery catheter diameter of 1–1.5 cm with a stent tightly wound around the catheter is sufficiently small to allow easy access with standard catheter insertion techniques. The stent illustrated in the drawings is a ribbon coiled stent. When heated to its high temperature state, the stent takes on the form of a helical coil of flat wire or ribbon, with the successive coils closely spaced, perhaps actually touching, to prohibit intrusion of swollen prostate tissue or sloughing tissue into the prostatic urethra. Closely spaced round wire coils may also be used, and other stent configurations such as expanded metal stents, braided stents and others may also be used.

Figure 9:
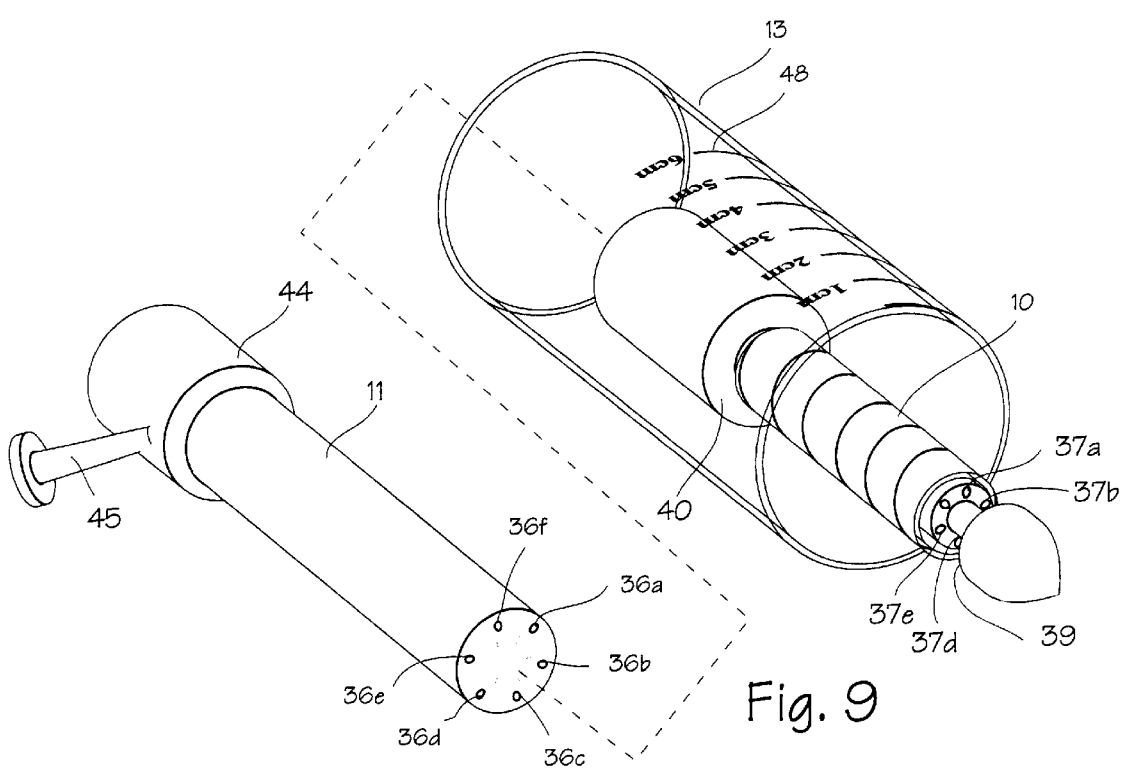

FIG. 9 illustrates a delivery catheter 11 with the stent 10 tightly wound about the catheter shaft. The catheter is a multi-lumen catheter, with lumens 36a, 36b, 36c, etc. communicating from the proximal end of the catheter to the distal end, with distal outlets 37a, 37b and 37c, etc.. With the stent in place around the catheter in the stent recess 38, which is a length of reduced cross section on the catheter between distal retaining shoulder 39 and proximal retaining shoulder 40. Forced flow of warm saline solution out the distal outlets 37 of lumens 36 will warm the stent and cause the distal end of the stent to change to its high temperature memorized shape. As the distal end expands, it will expand against the swollen prostate, and serve to anchor the distal end of the stent, ensuring proper placement of the entire stent whenever the distal end is properly placed. As water diffuses in the prostatic urethra, the more proximal areas of the stent will heat up and revert to the memorized shape, and the stent will expand radially, starting at the distal end and progressing to the proximal end, and thereby anchor itself into the prostatic urethra.

As illustrated in FIG. 10, the injection of saline may also be accomplished proximal end first, by providing additional lumens 41a, 41b, 41c, etc. and lumen outlets 42a, 42b, 42c, etc. in the distal end of the full diameter portion of the delivery catheter. These lumens will provide saline flow to the proximal end of the stent, so that the proximal end will be warmed first, expand and engage the prostate, and anchor the stent from the distal end. (Where an anchor section is provided, the anchor section may be deployed first). In either distal first or proximal first warming, once the end of the stent has expanded so that its diameter is larger than distal retaining shoulder 39 or proximal retaining shoulder 40, the delivery catheter can be moved proximally or distally to place the lumen outlets near unheated portions of the stent, thereby controlling expansion of the stent.

Various clinical factors, including successful visualization of the prostatic urethra, will determine whether a surgeon decides to employ proximal first or distal first deployment. The device may be manufactured to allow for one or the other, or for both simultaneously, or allow selective flow to outlets 37 or 42 during the deployment procedure. In FIG. 9, the proximal end 43 of the delivery catheter is fitted with a proximal hub 44 and a luer fitting 45, which provide an input port for saline solution to lumens 36. In FIG. 10, the hub is provide with an additional luer fitting 46 which provides saline flow to the additional lumens which communicate with a coaxial chamber in the hub communicating with proximal outlets of the lumens 41. Where it is desired to provide simultaneous flow paths to both the proximal outlets and the distal outlets, an additional luer fitting is unnecessary and a single chamber within the hub communicating with both sets of lumens 36 and 41 can be provided.

Catheter sheath 13 facilitates placement of the stent. The sheath is transparent and flexible. It is placed inside the urethra over an endoscope. The distal marking 47 is readily visible through the endoscope, as are ruled markings 48. The scope is inserted until the bladder neck sphincter is seen through the scope, and then the catheter sheath is advanced over the scope until the distal marking is visible and placed near the bladder neck sphincter. The endoscope is then pulled back until the external sphincter is located, and the ruled markings on the catheter sheath are used to measure the prostate gland so that a stent of appropriate size can be selected for use. The catheter sheath is left in place while the delivery catheter with a stent tightly wound upon the stent recess is inserted into the urethra through the catheter sheath. An endoscope is inserted either side-by-side with the stent, or within the stent as part of the delivery catheter. When the distal end of the stent is aligned with the desired point of deployment, just inside the prostate, downstream from the bladder neck sphincter, warm saline can be injected to cause expansion and deployment of the distal end of the stent.

Figure 11:
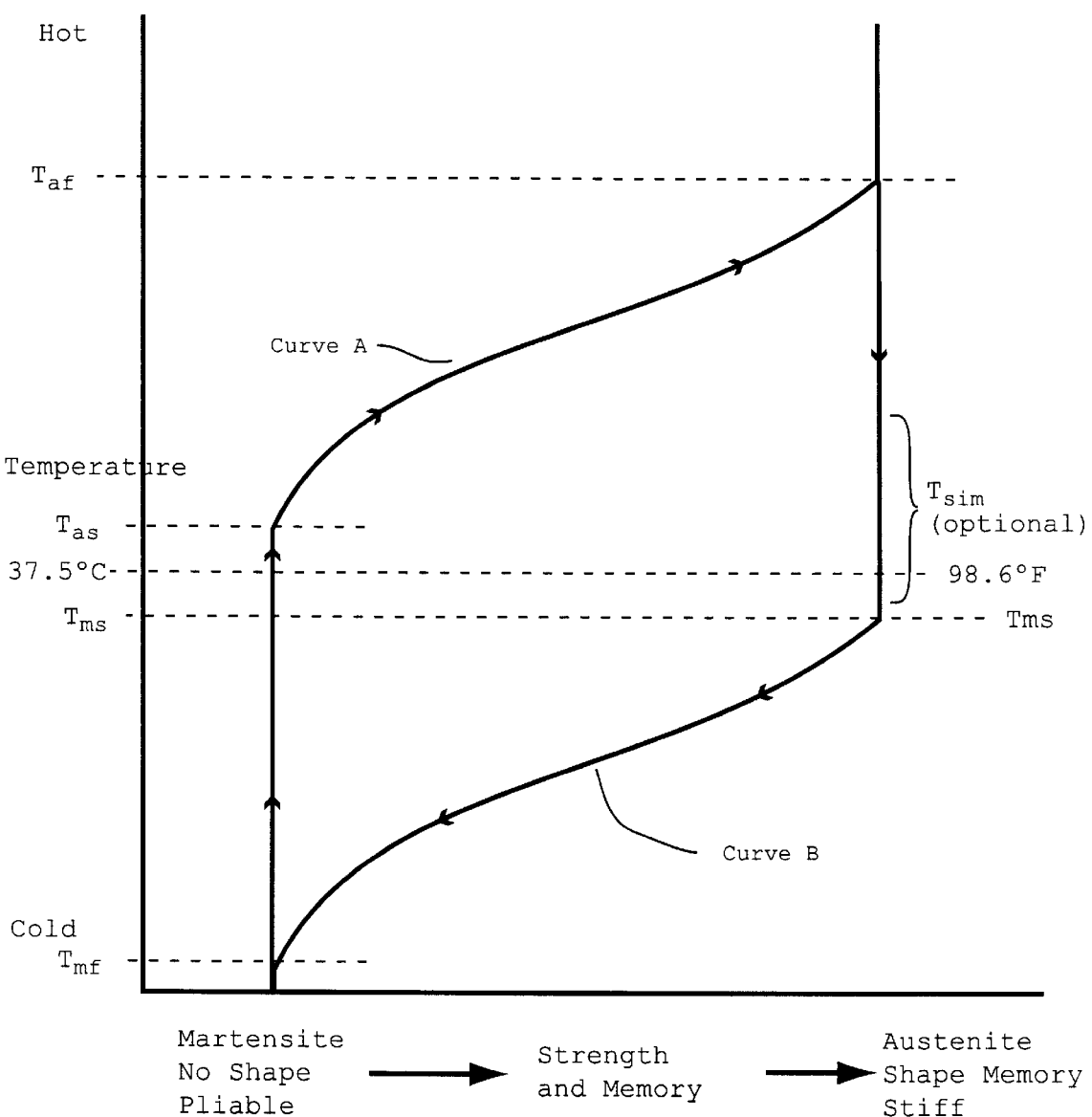
FIG. 11 is a graphical illustration of the stent's behavior in response to temperature changes.

FIG. 11 illustrates the metallurgical behavior of the stent. The stent is made of a shape memory alloy with a martensite state at cold temperature and an austenite state at high temperature, as is characteristic. Nitinol, comprised mostly of nickel and titanium, and usually alloyed with various other metals, is the most common shape memory alloy, however numerous alloys behave in similar fashion. At low temperature, the stent is in its martensite state, and is very pliable and has no memorized shape (except in alloys exhibiting two-way shape memory) and has very little strength. This is shown on the graph on curve A. As temperature rises, at a certain temperature (determined by a variety of factors, including composition of the alloy, readily controlled in the art of shape memory alloys) called the austenite start temperature, $T_{as}$, the metal starts to convert to austenite. The metal becomes stronger, stiffer, and reverts to its memorized shape as temperature increases to $T_{af}$. At the austenite finish temperature, $T_{af}$, the alloy has completely reverted to austenite, has recovered its memorized shape (unless restrained), and is stiff like spring steel. Above $T_{af}$, temperature increases do not affect the behavior of the metal (although it may distemper the metal and destroy its memory). Upon cooling, the metal reverts to the martensite state, but this does not occur exactly in reverse. The temperature at which reversion to martensite occurs upon cooling is lower than the temperature at which martensite-to-austenite conversion occurs. As shown in the graph, upon cooling to the martensite start temperature, $T_{ms}$, which is below body temperature, the metal start to become pliable. Further cooling to the martensite finish temperature $T_{mf}$ results in the complete conversion of the alloy to the soft, pliable martensite state. In the region on curve B above $T_{ms}$, the metal remains stiff and strong, even though the metal was soft and pliable at the same temperature upon heating on Curve A. Thus the alloy must be cooled considerably below the shape memory transition temperature $T_{af}$ before reversion back to the soft martensite state. The behavior is referred to as hysteresis, which is a term which generally refers to delays in changes of states of various systems. In some alloys, superelastic behavior occurs around the region of Curve B above $T_{ms}$. In this region, the metal may be substantially bent (deformed) but still spring back to its memorized shape, and this behavior is markedly different than normal metals. This region is shown on the graph as $T_{sim}$, which varies from alloy to alloy and might not be present in some alloys. Alloys and devices incorporating these characteristics may be manufactured according to known methods in the art of metallurgy.

These characteristics may be employed in the stent as follows. The stent is preferably made with an upward transition temperature (either $T_{as}$ or $T_{af}$) slightly above body temperature. The stent is also made with a downward transition temperature (either $T_{ms}$ or $T_{mf}$) below body temperature. The stent is trained using known techniques to memorize the high temperature shape illustrated above. Thus, once heated to cause the high temperature state with its memorized shape, the stent will remain in that shape at body temperature, and will hold the prostatic urethra open indefinitely. When it is desired to move the stent, cooling the stent with cold saline flow to a temperature below Tms causes it to revert to the cold pliable state, allowing easy deformation so that the stent may be pulled out of the urethra and into a catheter sheath. In alternate embodiments, superelasticity may be incorporated into the stent, so that if the stent is superelastic at body temperature, it may be restrained by the catheter sheath, inserted into the urethra and released by pulling the catheter away from the stent, allowing superelastic reversion to the memorized state. Two-way shape memory stents may also be used, such as those described in Harada, wherein the stent is fabricated to have a memorized shape at high temperature and at low temperature, wherein injection of cold saline around the stent causes reversion to a low temperature memory shape with a small diameter. However, given the expected shrinkage of the prostate gland in response to therapy, the prostate will already be receding from the stent, and it is possible to remove a one-way memory stent in this environment. Thus, two-way shape memory is not necessary in the normal prostatic treatment case.

While the preferred embodiments of the devices and methods have been described, they are merely illustrative of the principles of the invention. Other embodiments and configurations may be devised without departing from the spirit of the inventions and the scope of the appended claims. While the inventions have been described in the environment of urology, the application of the inventive concepts in other areas of heat therapy and temporary stent application will be beneficial. It is specifically contemplated that the materials employed in the illustrated embodiments be improved upon, that methods and patterns of irradiation and heating of the stent be improved upon, and that the time tables for therapy discussed above be improved upon, and that all such improvements fall within the scope of the claims.

We claim:

1. A stent for use within the prostatic urethra, said stent comprising:

a length of flat wire comprised of a shape memory metal having a high temperature state in which the shape memory metal is trained to revert to the shape of a helical coil, and a low temperature state in which the metal is easily deformable;

wherein said low temperature state occurs when the stent is cooled to temperatures below body temperature, and said low temperature state is retained upon heating to body temperature, and the high temperature state occurs when the stent is heated to temperatures above body temperature and said high temperature state is retained upon cooling to body temperature.

2. A stent for use within the prostatic urethra, said stent comprising:

a length of flat wire comprised of a shape memory metal having a high temperature austenite state in which the shape memory metal is trained to revert to the shape of a helical coil, and a low temperature martensite state in which the metal is easily deformable;

wherein said low temperature martensite state occurs when the stent is cooled to temperatures below body temperature, and said low temperature martensite state is retained upon heating to body temperature, and the high temperature austenite state occurs when the stent is heated to temperatures above body temperature and said high temperature austenite state is retained upon cooling to body temperature.

3. The device of claim 2 wherein the high temperature state is achieved upon heating to a temperature range of about 38–60° C., and the low temperature martensite state is achieved upon cooling to the temperature range of 30–35° C.

* * * * *